(12) United States Patent
Prandi et al.

(10) Patent No.: US 8,579,898 B2
(45) Date of Patent: Nov. 12, 2013

(54) ADJUSTABLE-ANGLE RADIUS PLATE

(75) Inventors: Bernard Prandi, Rennes (FR); Gregoire Chick, Carouge (CH); Jean Michel Cognet, Reims (FR); Xavier Martinache, Reims (FR); Michaël Papaloïzos, Geneva (CH); Alain Tchurukdichian, Dijon (FR)

(73) Assignee: Memometal Technologies (FR)

( * ) Notice: Subject to any disclaimer, the term of this patent is extended or adjusted under 35 U.S.C. 154(b) by 122 days.

(21) Appl. No.: 12/948,809

(22) Filed: Nov. 18, 2010

(65) Prior Publication Data

US 2011/0218534 A1 Sep. 8, 2011

(30) Foreign Application Priority Data

Mar. 8, 2010 (FR) ..................... 10 00937

(51) Int. Cl.
*A61B 17/56* (2006.01)
*A61B 17/58* (2006.01)
*A61B 17/80* (2006.01)
*A61F 2/30* (2006.01)

(52) U.S. Cl.
USPC ............................. 606/71; 606/280; 606/70

(58) Field of Classification Search
USPC ..................... 606/280–299, 70, 71
See application file for complete search history.

(56) References Cited

U.S. PATENT DOCUMENTS

| | | | |
|---|---|---|---|
| 2,526,959 A | 10/1950 | Lorenzo | |
| 2,580,821 A | 1/1952 | Nicola | |
| 3,304,937 A * | 2/1967 | Callender, Jr. | ................. 602/25 |
| 3,386,437 A | 6/1968 | Treace | |
| 3,488,779 A | 1/1970 | Christensen | |
| 3,489,143 A | 1/1970 | Halloran | |
| 3,604,414 A * | 9/1971 | Borges | .......................... 606/105 |
| 3,842,825 A | 10/1974 | Wagner | |
| 3,900,025 A | 8/1975 | Barnes, Jr. | |
| 4,454,876 A | 6/1984 | Mears | |
| 4,506,662 A | 3/1985 | Anapliotis | |
| 4,867,144 A | 9/1989 | Karas et al. | |
| 4,988,350 A | 1/1991 | Herzberg | |

(Continued)

FOREIGN PATENT DOCUMENTS

| | | | |
|---|---|---|---|
| EP | 0362049 A1 | 4/1990 | |
| EP | 0410309 A1 | 1/1991 | |

(Continued)

*Primary Examiner* — Kevin T Truong
*Assistant Examiner* — Si Ming Lee
(74) *Attorney, Agent, or Firm* — Lerner, David, Littenberg, Krumholz & Mentlik, LLP

(57) ABSTRACT

A bone plate for a fracture between an epiphysis and a diaphysis has an outer part unitarily formed with a fan-shaped outer end having a plurality of outer holes and an inner end extending from the outer end. A bar-shaped inner part has an outer end juxtaposed with the inner end of the outer part and formed inward of its outer end with a plurality of inner holes. A pivot is provided between the inner end of the outer part and the outer end of the inner part. Formations juxtaposed with the pivot on the inner end of the outer part and on the outer end of the inner part are lockable together in each of a plurality of angularly offset fixed positions of the inner and outer parts. When the formations are pressed together the inner and outer parts are locked angularly relative to each other.

9 Claims, 3 Drawing Sheets

(56) References Cited

U.S. PATENT DOCUMENTS

| | | |
|---|---|---|
| 5,006,120 A | 4/1991 | Carter |
| 5,041,113 A | 8/1991 | Biedermann et al. |
| 5,197,966 A | 3/1993 | Sommerkamp |
| 5,304,180 A | 4/1994 | Slocum |
| 5,324,290 A | 6/1994 | Zdeblick et al. |
| 5,380,327 A | 1/1995 | Eggers et al. |
| 5,462,547 A | 10/1995 | Weigum |
| 5,474,553 A | 12/1995 | Baumgart |
| 5,487,743 A | 1/1996 | Laurain et al. |
| 5,531,745 A | 7/1996 | Ray |
| 5,586,985 A | 12/1996 | Putnam et al. |
| 5,665,089 A | 9/1997 | Dall et al. |
| 5,681,313 A | 10/1997 | Diez |
| 5,749,872 A | 5/1998 | Kyle et al. |
| 5,827,286 A | 10/1998 | Incavo et al. |
| 5,853,413 A | 12/1998 | Carter et al. |
| 5,928,234 A | 7/1999 | Manspeizer |
| 5,951,557 A | 9/1999 | Luter |
| 5,964,763 A | 10/1999 | Incavo et al. |
| 5,968,047 A | 10/1999 | Reed |
| 6,007,535 A | 12/1999 | Rayhack et al. |
| 6,096,040 A | 8/2000 | Esser |
| 6,129,728 A | 10/2000 | Schumacher et al. |
| 6,183,475 B1 | 2/2001 | Lester et al. |
| D443,060 S | 5/2001 | Benirschke et al. |
| 6,283,969 B1 | 9/2001 | Grusin et al. |
| 6,306,136 B1 | 10/2001 | Baccelli |
| 6,325,803 B1 | 12/2001 | Schumacher et al. |
| 6,355,036 B1 | 3/2002 | Nakajima |
| 6,358,250 B1 | 3/2002 | Orbay |
| 6,364,882 B1 | 4/2002 | Orbay |
| 6,402,756 B1 | 6/2002 | Ralph et al. |
| 6,440,135 B2 | 8/2002 | Orbay et al. |
| 6,508,819 B1 | 1/2003 | Orbay |
| 6,623,486 B1 | 9/2003 | Weaver et al. |
| 6,666,867 B2 | 12/2003 | Ralph et al. |
| 6,689,134 B2 | 2/2004 | Ralph et al. |
| 6,712,820 B2 | 3/2004 | Orbay |
| 6,740,088 B1 | 5/2004 | Kozak et al. |
| 6,755,831 B2 | 6/2004 | Putnam et al. |
| 6,767,351 B2 | 7/2004 | Orbay et al. |
| 6,866,665 B2 | 3/2005 | Orbay |
| 7,090,676 B2 * | 8/2006 | Huebner et al. ................. 606/71 |
| 7,128,744 B2 | 10/2006 | Weaver et al. |
| 7,189,237 B2 | 3/2007 | Huebner |
| 7,201,753 B2 | 4/2007 | Schlaepfer |
| 7,250,053 B2 | 7/2007 | Orbay |
| 7,276,070 B2 | 10/2007 | Muckter |
| 7,294,130 B2 | 11/2007 | Orbay |
| 7,326,212 B2 | 2/2008 | Huebner |
| 7,537,604 B2 | 5/2009 | Huebner |
| 7,604,657 B2 | 10/2009 | Orbay et al. |
| 7,635,381 B2 | 12/2009 | Orbay |
| 7,648,508 B2 | 1/2010 | Lutz et al. |
| 7,695,502 B2 | 4/2010 | Orbay et al. |
| 7,704,251 B2 | 4/2010 | Huebner et al. |
| 7,740,649 B2 | 6/2010 | Mosca et al. |
| 7,744,638 B2 | 6/2010 | Orbay |
| 7,857,837 B2 | 12/2010 | Lieponis |
| 7,857,838 B2 | 12/2010 | Orbay |
| 7,867,260 B2 | 1/2011 | Meyer et al. |
| 7,909,858 B2 | 3/2011 | Gerlach et al. |
| 7,914,562 B2 | 3/2011 | Zielinski |
| 2001/0011172 A1 | 8/2001 | Orbay et al. |
| 2002/0032446 A1 | 3/2002 | Orbay |
| 2002/0055741 A1 | 5/2002 | Schlapfer et al. |
| 2002/0065517 A1 | 5/2002 | Paul |
| 2002/0111630 A1 | 8/2002 | Ralph et al. |
| 2002/0143338 A1 | 10/2002 | Orbay et al. |
| 2002/0147453 A1 | 10/2002 | Gambale |
| 2002/0156474 A1 | 10/2002 | Wack et al. |
| 2003/0040748 A1 | 2/2003 | Aikins et al. |
| 2003/0055429 A1 | 3/2003 | Ip et al. |
| 2003/0073999 A1 | 4/2003 | Putnam |
| 2003/0105461 A1 | 6/2003 | Putnam |
| 2003/0149434 A1 | 8/2003 | Paul |
| 2003/0153918 A1 | 8/2003 | Putnam et al. |
| 2003/0233093 A1 | 12/2003 | Moles et al. |
| 2004/0030339 A1 | 2/2004 | Wack et al. |
| 2004/0059334 A1 | 3/2004 | Weaver et al. |
| 2004/0059335 A1 | 3/2004 | Weaver et al. |
| 2004/0102775 A1 | 5/2004 | Huebner |
| 2004/0102776 A1 | 5/2004 | Huebner |
| 2004/0102777 A1 | 5/2004 | Huebner |
| 2004/0102778 A1 | 5/2004 | Huebner et al. |
| 2004/0106924 A1 | 6/2004 | Ralph et al. |
| 2004/0116930 A1 | 6/2004 | O'Driscoll et al. |
| 2004/0127903 A1 | 7/2004 | Schlapfer et al. |
| 2004/0153073 A1 | 8/2004 | Orbay |
| 2004/0167522 A1 | 8/2004 | Niederberger et al. |
| 2004/0181226 A1 | 9/2004 | Michelson |
| 2004/0193155 A1 | 9/2004 | Castaneda |
| 2004/0193163 A1 | 9/2004 | Orbay |
| 2004/0193164 A1 | 9/2004 | Orbay |
| 2004/0193165 A1 | 9/2004 | Orbay |
| 2004/0204713 A1 | 10/2004 | Abdou |
| 2004/0260292 A1 | 12/2004 | Orbay et al. |
| 2004/0260293 A1 | 12/2004 | Orbay et al. |
| 2004/0260294 A1 | 12/2004 | Orbay et al. |
| 2004/0260295 A1 | 12/2004 | Orbay et al. |
| 2005/0010226 A1 | 1/2005 | Grady et al. |
| 2005/0065521 A1 | 3/2005 | Steger et al. |
| 2005/0065522 A1 | 3/2005 | Orbay |
| 2005/0065523 A1 | 3/2005 | Orbay |
| 2005/0065524 A1 | 3/2005 | Orbay |
| 2005/0080421 A1 | 4/2005 | Weaver et al. |
| 2005/0085818 A1 | 4/2005 | Huebner |
| 2005/0159747 A1 | 7/2005 | Orbay |
| 2005/0165395 A1 | 7/2005 | Orbay et al. |
| 2005/0182405 A1 | 8/2005 | Orbay et al. |
| 2005/0182406 A1 | 8/2005 | Orbay et al. |
| 2005/0234458 A1 | 10/2005 | Huebner |
| 2005/0240186 A1 | 10/2005 | Orbay |
| 2005/0240187 A1 | 10/2005 | Huebner et al. |
| 2005/0267474 A1 | 12/2005 | Dalton |
| 2006/0089648 A1 | 4/2006 | Masini |
| 2006/0173458 A1 | 8/2006 | Forstein et al. |
| 2006/0229619 A1 | 10/2006 | Orbay |
| 2006/0235404 A1 | 10/2006 | Orbay |
| 2006/0259039 A1 | 11/2006 | Pitkanen et al. |
| 2006/0264949 A1 | 11/2006 | Kohut et al. |
| 2007/0055253 A1 | 3/2007 | Orbay et al. |
| 2007/0123886 A1 | 5/2007 | Meyer et al. |
| 2007/0162016 A1 | 7/2007 | Matityahu |
| 2007/0233114 A1 | 10/2007 | Bouman |
| 2007/0239163 A1 | 10/2007 | Strnad et al. |
| 2007/0265629 A1 | 11/2007 | Martin et al. |
| 2007/0270853 A1 | 11/2007 | Leung |
| 2007/0299448 A1 | 12/2007 | Chin et al. |
| 2008/0132960 A1 | 6/2008 | Weaver et al. |
| 2008/0140127 A1 | 6/2008 | Vasta et al. |
| 2008/0140130 A1 | 6/2008 | Chan et al. |
| 2008/0161861 A1 * | 7/2008 | Huebner ....................... 606/286 |
| 2008/0183172 A1 | 7/2008 | Fritzinger |
| 2008/0195240 A1 | 8/2008 | Martin et al. |
| 2009/0036931 A1 | 2/2009 | Pech et al. |
| 2009/0036932 A1 | 2/2009 | Rouyer et al. |
| 2009/0082813 A1 | 3/2009 | Long et al. |
| 2009/0118768 A1 | 5/2009 | Sixto, Jr. et al. |
| 2009/0118769 A1 | 5/2009 | Sixto, Jr. et al. |
| 2009/0118770 A1 | 5/2009 | Sixto, Jr. et al. |
| 2009/0143825 A1 | 6/2009 | Graham et al. |
| 2009/0228047 A1 | 9/2009 | Derouet et al. |
| 2009/0234359 A1 | 9/2009 | Onoue et al. |
| 2009/0275947 A1 * | 11/2009 | Graham et al. ................. 606/71 |
| 2009/0275987 A1 | 11/2009 | Graham et al. |
| 2009/0281577 A1 | 11/2009 | Graham et al. |
| 2009/0281578 A1 | 11/2009 | Spencer |
| 2009/0299370 A1 | 12/2009 | Kiester |
| 2009/0306724 A1 | 12/2009 | Leither et al. |
| 2009/0326591 A1 | 12/2009 | Spencer, Jr. |
| 2010/0016858 A1 | 1/2010 | Michel |
| 2010/0030276 A1 | 2/2010 | Huebner et al. |
| 2010/0030277 A1 | 2/2010 | Haidukewych et al. |

(56) References Cited

U.S. PATENT DOCUMENTS

| | | |
|---|---|---|
| 2010/0057132 A1 | 3/2010 | Graham et al. |
| 2010/0057133 A1 | 3/2010 | Simon |
| 2010/0057134 A1 | 3/2010 | Lowry et al. |
| 2010/0063505 A1 | 3/2010 | Frigg et al. |
| 2010/0069906 A1 | 3/2010 | Schwer |
| 2010/0137868 A1 | 6/2010 | Orbay et al. |
| 2010/0152783 A1 | 6/2010 | Borostyankoi et al. |
| 2010/0179599 A1 | 7/2010 | Derouet et al. |
| 2010/0268283 A1 | 10/2010 | Orbay |
| 2010/0292696 A1 | 11/2010 | Chantelot et al. |
| 2010/0324602 A1 | 12/2010 | Huebner et al. |
| 2011/0004252 A1 | 1/2011 | Velikov |
| 2011/0071573 A1 | 3/2011 | Sixto et al. |

FOREIGN PATENT DOCUMENTS

| | | |
|---|---|---|
| EP | 0471418 A1 | 2/1992 |
| EP | 1 250 892 A2 | 10/2002 |
| FR | 742618 A | 3/1933 |
| FR | 2254298 A1 | 7/1975 |
| FR | 2367479 A1 | 5/1978 |
| FR | 2405705 A1 | 5/1979 |
| FR | 2405706 A1 | 5/1979 |
| FR | 2406429 A1 | 5/1979 |
| GB | 2245498 A | 1/1992 |
| JP | 9206310 A | 8/1997 |
| SU | 1130332 A1 | 12/1984 |
| SU | 1223901 A1 | 4/1986 |
| SU | 1683724 A1 | 10/1991 |
| SU | 1711859 A1 | 2/1992 |
| SU | 1734715 A1 | 5/1992 |
| WO | 8201645 A1 | 5/1982 |
| WO | 9747251 A1 | 12/1997 |
| WO | 0162136 A2 | 8/2001 |
| WO | 2004089233 A | 2/2004 |
| WO | 2004045389 A2 | 6/2004 |
| WO | 2008113191 A1 | 9/2008 |

* cited by examiner

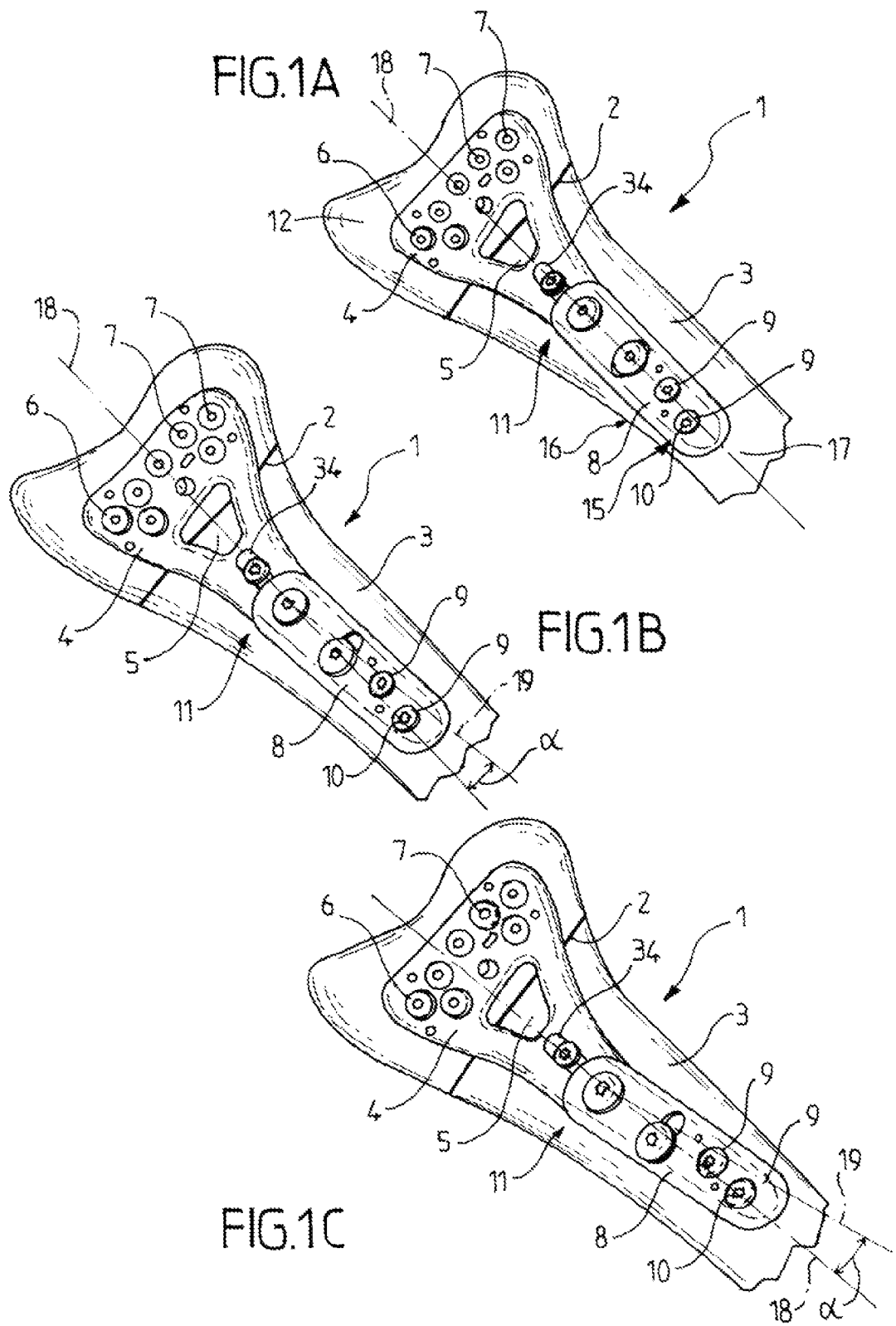

ADJUSTABLE-ANGLE RADIUS PLATE

FIELD OF THE INVENTION

The present invention relates to a bone plate. More particularly this invention concerns such a plate used to splint a fracture between the epiphysis and diaphysis of a long bone such as the radius.

BACKGROUND OF THE INVENTION

A typical bone plate such as described in WO 2004/089233 of Thielke, US 2006/0229619 of Orbay, US 2006/0235404, or US 2007/0055253 all of Orbay, extends along an axis and has an outer end that is fan-shaped and formed with an array of holes so that it can be solidly screwed to the epiphysis or bone head to one side of the fracture or other injury that is to be reduced so the bone can grow back together. Extending from this fan-shaped outer end is a flat narrow bar formed with another array of holes allowing it to be screwed to the bone's shaft or diaphysis. The most common use of such a bone plate is in setting or reducing a distal fracture of the radius, but it can of course also be used for any type of fracture on a distal portion of a long bone.

Such a bone plate is used to hold the broken bone together at the fracture so that by arthrodesis the bone will knit back together. Once the fracture has mended the plate may be removed. Such a plate allows for a faster reduction of the break by biasing it together, to prevent later phenomena such as arthrosis.

In the case of distal fractures of the radius, plates allowing for a positioning in length by means of an oblong hole are already known. Such plates, which return the distal fragment to the correct spacing and fix it by adjusting the plate in length before it is locked in the diaphysis, do not however enable any lateral adjustment. The bone plate of US 2007/0233114 of Bouman has transverse and longitudinal slots allowing some longitudinal and transverse relative shifting of parts, but in a structure intended for use on a bone shaft.

Because of the exigencies of surgery, in some cases it is necessary to first fix the distal fragments of the radius on the plate before the fracture is reduced on the diaphysis.

One can, however, never be sure of the orientation of the plate, which therefore is not always on the axis of the radius. In this case the elongated diaphysial or inner portion of the broken bone might be offset transversely and thus make the patient uncomfortable. The surgeon cannot correct this slight lateral positioning defect without repositioning the epiphysial part of the bone plate, which requires redrilling near the first holes so as to be offset. In practice, this is not possible since the holes are too close to each other, plus the surgical procedure is made longer and more complex, and more damage is done to the epiphysis.

It has therefore been suggested in US 2006/0089648 of Masini and U.S. Pat. No. 7,090,676 of Huebner to separate outer and inner parts of such a bone plate and pivot them together so their relative angular positions can be adjusted. These systems offer some improvement, but have the considerable disadvantage that they frequently fail in use, with the two parts, even if screwed tightly to each other during surgery, loosening and allowing the fracture to work, thereby impeding healing. The problem is that the bone plate is subjected to considerable mechanical action during and after surgery, but is of course totally inaccessible once the surgical field is closed. Thus the procedure of, for example, applying a cast might be enough to loosen it and basically make it useless.

OBJECTS OF THE INVENTION

It is therefore an object of the present invention to provide an improved bone plate.

Another object is the provision of such an improved bone plate that overcomes the above-given disadvantages, in particular that better fulfills the requirements of the practice than those known in the prior art, particularly by allowing for reorienting the elongated diaphysial part of the bone plate largely regardless of any minor misalignment of the position of the epiphysial or outer part in the initial fixing of the epiphysial part during the surgery.

SUMMARY OF THE INVENTION

A bone plate for reducing a fracture between an epiphysis and a diaphysis of a bone has according to the invention an outer part unitarily formed with a fan-shaped outer end formed with a plurality of outer holes and an inner end extending along a longitudinal axis from the outer end. The outer part is adapted to be screwed through the outer holes to the epiphysis. A bar-shaped inner part has an outer end juxtaposed with the inner end of the outer part and formed inward of its outer end with a plurality of inner holes. The inner part is adapted to be screwed through the inner holes to the diaphysis. A pivot between the inner end of the outer part and the outer end of the inner part defines a pivot axis. Formations juxtaposed with the pivot on the inner end of the outer part and on the outer end of the inner part are lockable together in each of a plurality of angularly offset fixed positions of the inner and outer parts. When the formations are pressed together the inner and outer parts are locked angularly relative to each other Naturally, the invention can be used for any type of fracture of the end of an elongated or long bone, or osteosynthesis, and not only on a radius end.

The fact that the diaphysial part of the plate can be positioned so as to be adjustably fixed with respect to the fan-shaped distal part makes it possible to prevent a lateral overextension with respect to the body of the bone. Such an overextension which would have caused the patient to be uncomfortable.

The term blockable articulation refers to an articulation which allows for an orientation adjustment which, once the desired position has been chosen, makes it possible to rigidly block the two parts with respect to each other.

The outer or epiphysial part can pivot relative to the inner or diaphysial part according to the invention through about 30°, that is ±15° from a center position with a center axis of the outer part aligned with or parallel to the center axis of the inner part. The variation can be for example 5° to 15°, and advantageously between 8° and 10°. The fact that the two parts can be locked at an angle to each other. The two defined angle values in the diaphysial plane are +15° and −15° with respect to the central alignment position, making a number of the angular positions between the two values possible in a steps. The extreme values can also be less, for example +10° and −10°.

The epiphysial and diaphysial parts are separable from each other. In other words, they are not structurally fixed to each other but rather separable from each other before they are assembled and fixed to each other.

Each the epiphysial and diaphysial parts comprises an end for joining it to the other part and having a face for cooperating with each other, and means for rotationally locking these ends with respect to each other. The overlapping ends are thinner than the rest of the assembly so it is of the same thickness where the inner end of the outer part overlaps the outer end of the inner part as elsewhere. The locking means consists of two arrays of teeth facing each other, each fixed to one end, and fittable complementarily together to block rotation when held together by a screw. Minor loosening of the screw is not sufficient to allow the parts to relatively rotate as in the prior art.

In other words, the junction ends have identical toothed formations facing each other and can only relative rotate when spaced apart from each other. Blocking being achieved when they are brought engaged and in contact with each other, so that the teeth of the two faces facing each other interengage. The blocking is carried out by means of a screw in a known manner.

One of the ends has a screw seat facing a slot in the other end with which it slidingly cooperates, and a screw for fixing the stud on the other end through this slot. This screw allows the two parts to be fixed angularly relative to each other during installation, before the screw at the pivot axis is tightened to engage the teeth together and lock in the selected position.

The screws used are arranged so as to lock themselves at the end of the travel to prevent any migration, in a known manner. This can be done by lock washers or formations under the screw heads.

BRIEF DESCRIPTION OF THE DRAWING

The above and other objects, features, and advantages will become more readily apparent from the following description, reference being made to the accompanying drawing in which:

FIGS. 1A, 1B, and 1C show the adjustable plate according to the invention in three different angular positions, respectively at 0°, at 5°, and at 10° with respect to a central alignment position;

SPECIFIC DESCRIPTION

Figure 2A:
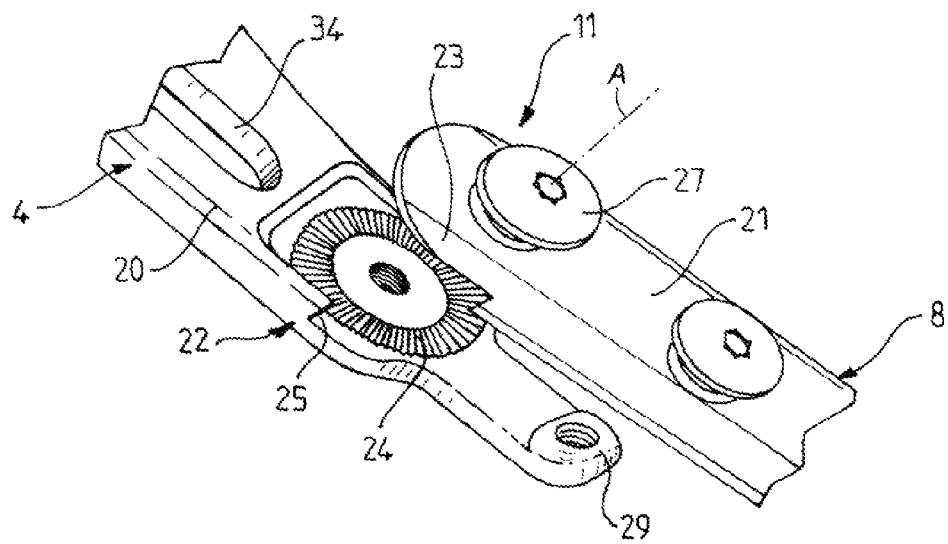
FIGS. 2A and 2B are perspective exploded top and bottom views of the ends of the junction between the parts showing the rotation-blocking means according to the invention.

As seen in the drawing, an osteosynthesis plate 1 is used for reducing a distal fracture 2 of a radius 3. The plate 1 comprises a fan-shaped epiphysial or outer part 4 here formed with a central window 5 through which the fracture 2 can be viewed. The epiphysial part 4 is provided with outer holes 6 at which it is secured to the epiphysis 12 of the bone 3 by anchor screws 7 in a known manner. Another slot 34 is formed in the outer part 4, lying on a midline 18 thereof and used as described in more detail below. The plate 1 also comprises an elongated or bar-shaped diaphysial or inner part 8 formed with a row of inner holes 9 through which it is securable to the shaft or diaphysis 17 of the bone 3 by inner anchor screws 10.

According to the embodiment described more particularly here, the plate 1 further comprises a hinge or pivot 11 between the two parts 4 and 8 and allowing them to relatively pivot about an axis A (FIG. 2A) of ±15°. More precisely, FIGS. 1A to 1C show the epiphysial and diaphysial parts 4 and 8 when they are in the central aligned position (FIG. 1A), at a 5° angle α (FIG. 1B), or a 10° angle α (FIG. 1C).

With central alignment (FIG. 1A), a side edge 15 of the diaphysial part 8 is very close to an edge 16 of the diaphysis 17 of the bone 3, which can cause some discomfort to the patient. In the position of FIG. 1B, the angle α between a central alignment axis 18 of the outer part 4, with an axis 19 of the diaphysial part 8 is a 5° angle, and a 10° angle in the position of FIG. 1C.

Figure 2B:
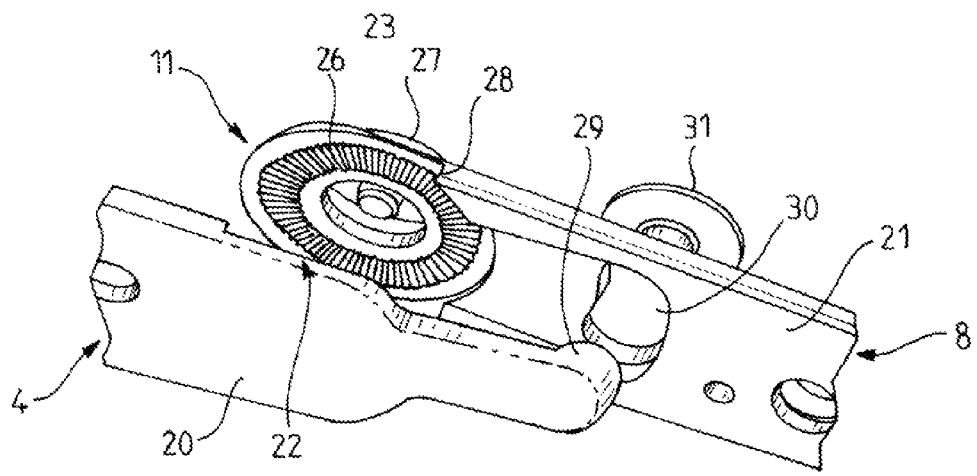

FIGS. 2A and 2B show more precisely the hinge or pivot 11 of FIG. 1 between an inner end 20 of the outer part 4 and an outer end 21 of the inner part 8. The ends 20 and 21 are both of reduced thickness in overlapping portions 22 and 23 so as not to add to the thickness of the plate 1. The end 20 is formed centered on the axis A with an annular array of radially extending ridges or teeth 24 and with a pair of abutments 25 defining the limits of relative pivoting of the parts 4 and 8. The other end 21 is similarly formed centered on the axis with an array of radially extending ridges or teeth 26 complementary to the teeth 25 and fittable therewith to define when fitted together a multiplicity of angularly offset positions of the two parts 4 and 8. A screw 27 projects on the axis through the one end 21 into a threaded hole on the other end 20 so that, when tightened, it can lock the teeth 24 in the teeth 26 in one of the positions. The end 21 also has two abutments 28 engageable with the abutments 25 when the angularly offset end positions are reached at +15° or −15°, for example.

Inward of the axis A, a projection of the end 20 further forms a threaded seat 29 in which a screw 31 can engage. This screw 31 in turn engages through an arcuate slot 30 formed in the end 21 so that, when tightened, it presses the ends 20 and 21 together at a location offset from the axis A. When both the screws 27 and 31 are tightened, the parts 4 and 8 are locked very solidly together, the screw 31 serving mainly for stabilization during installation. The screws 27 and 31 are made to lock when tightened home, for instance by a lock washer or lock formation under their screw heads.

FIGS. 3A-3D show the installation of the plate 1 in more detail:

First, (FIG. 3A), the plate 1 is set in place on the epiphysial part 12 of the bone, which is particularly useful in case of a fracture 2. The epiphysial part 4 is fixed by the anchor screws 7 adjusted as well as possible to site conditions.

Then (FIG. 3B) the fracture 2 is reduced by bringing closer together the fractured epiphysial portion 12 and the diaphysis 17 of the bone 3. But at this stage, one does not really check the position of the longitudinal axis 18.

Figure 3A:
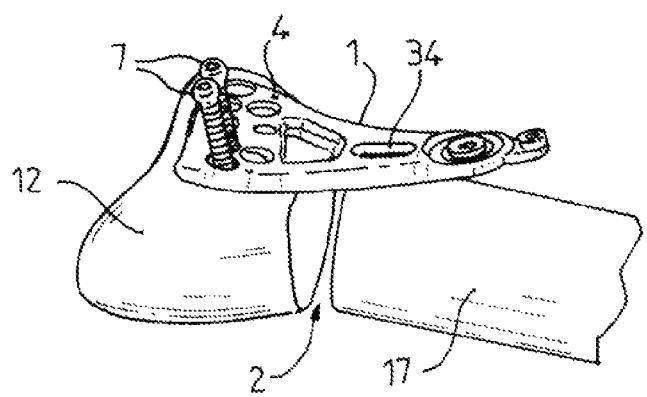
FIGS. 3A to 3D show the successive steps for setting in place an osteosynthesis plate according to the embodiment in FIG. 1.
Figure 3B:
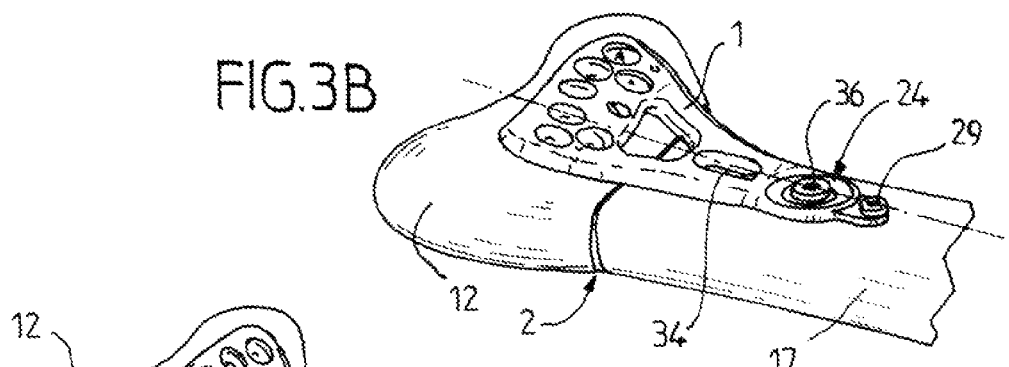
Figure 3C:
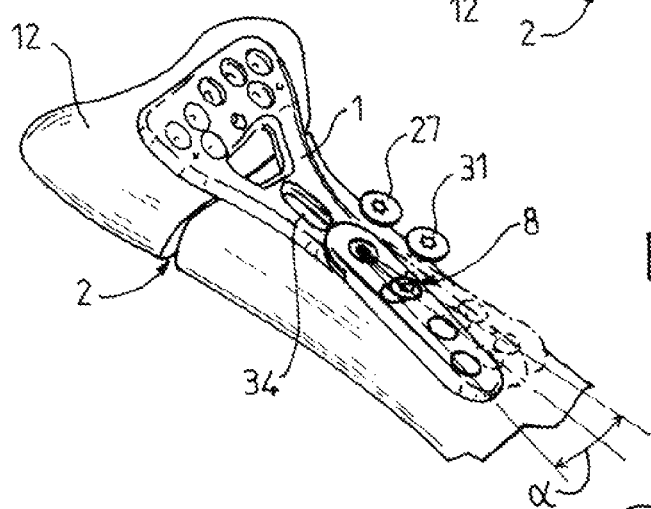
Figure 3D:
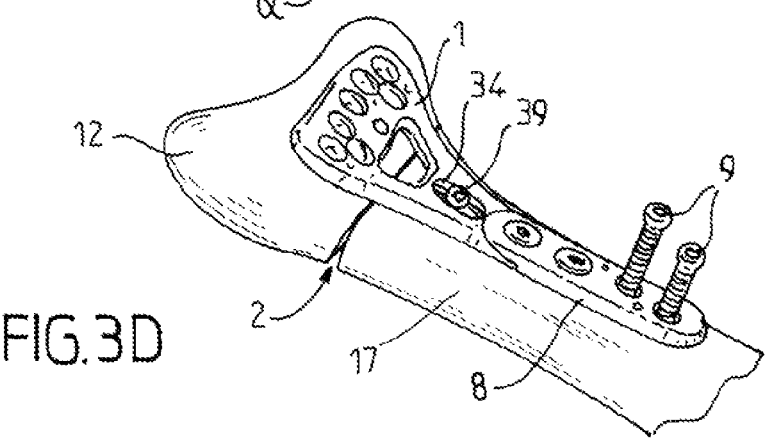

As shown in FIG. 3B only the part 4 is secured to the head 12 of the bone 3 to start with Then, (FIG. 3C), the diaphysial part 8 is set on the part 12 with its teeth 26 meshing with the teeth 24 of the part 4, regardless whether the part 8 is aligned with the axis 18. What is important is that it is aligned with the diaphysis 17. Once it is correctly positioned, it is locked in the desired angular position by the two screws 27 and 31 described above.

Finally, (FIG. 3D) the longitudinal position is refined by inserting a screw through the slot 34 into the diaphysis 17 and, with the fracture 2 reduced, tightening it, and then screws 10 are driven through the holes 9

By way of nonlimiting example, the length of the screw 27 is of 5 to 10 mm, the depth of the notches or height of the teeth 24 and 26 on the order of 0.2 mm, the number of notches being comprised between 50 and 100 for a length of 10 to 15 mm of the thin portions 22 and 23.

It goes without saying and it results from what precedes that the present invention is not limited to the embodiment more particularly described here. To the contrary, it encompasses all the alternatives and particularly those where the angles are not ±15°, but ±10° and/or ±20°, the one where the epiphysial part and the diaphysial part are different from those described and/or are made of different materials, those where there are two studs facing two slots, respectively, located in the other end, with which they slidingly cooperate, namely a stud on the epiphysial part and a stud on the diaphysial part, and a slot on the facing portions, the studs (and therefore the slots) being located on both sides, for example symmetrically of the rotation axis of the articulation and locking themselves with fixing screws of the stud through the corresponding slot.

We claim:

1. A bone plate for reducing a fracture between an epiphysis and a diaphysis of a bone, the plate comprising:
   an outer part unitarily formed with a fan-shaped outer end formed with a plurality of outer holes and an inner end extending along a longitudinal axis from the outer end, the outer part being adapted to be screwed through the outer holes to the epiphysis;
   a bar-shaped inner part having an outer end juxtaposed with the inner end of the outer part and a plurality of inner holes formed inwardly of the outer end thereof, the inner part being adapted to be screwed through the inner holes to the diaphysis, the outer end of the inner part having a throughgoing slot positioned over an extension of the inner end of the outer part, the throughgoing slot having a longest dimension in a direction transverse to the longitudinal axis, the extension projecting under the outer end of the inner part and including a circular screw seat on an end thereof;
   a pivot between the inner end of the outer part and the outer end of the inner part and defining a pivot axis;
   formations juxtaposed with the pivot and lockable together in each of a plurality of angularly offset fixed positions of the inner and outer parts;
   means for pressing the formations together and thereby locking the inner and outer parts at various angles relative to each other in each of the positions; and
   a screw having a shaft seated in the screw seat and a head engaging the outer end of the inner part, the screw shaft and the screw seat being dimensioned for engagement with each other around entire circumferences thereof;
   wherein the throughgoing slot is sized to permit engagement of the screw with the outer part through the throughgoing slot during relative pivoting of the outer and inner parts.

2. The bone plate defined in claim 1 wherein the formations on the inner end of the outer part are an array of teeth extending radially of the pivot axis and projecting axially of the pivot toward the outer end of the inner part, the formations on the outer end of the inner part being a complementary array of teeth axially meshable with the teeth of the outer part.

3. The bone plate defined in claim 1 wherein the means for pressing includes a screw having a shaft threaded axially into the inner end of the outer part and a head bearing axially on the outer end of the inner part.

4. The bone plate defined in claim 1 a total thickness of the outer end of the inner part and the inner end of the outer part is the same thickness as elsewhere on the bone plate.

5. The bone plate defined in claim 1 wherein the inner end of the outer part is formed with a throughgoing slot extending generally parallel to the diaphysis, the plate further comprising an anchor screw extending through the slot and seated in the diaphysis.

6. The bone plate defined in claim 1 wherein the outer part is formed between its inner and outer ends with a window through which a fracture between the diaphysis and epiphysis is viewable.

7. The bone plate defined in claim 1, further comprising abutments on the inner and outer parts limiting pivoting of the inner part to an angle of 30° about the pivot axis relative to the outer part.

8. The bone plate defined in claim 1, wherein the inner and outer parts are assembled at the pivot.

9. The bone plate defined in claim 1, wherein the throughgoing slot is arcuate such that the screw may be translated along an arcuate path.

* * * * *